(12) United States Patent
Lynch et al.

(10) Patent No.: US 7,361,330 B2
(45) Date of Patent: Apr. 22, 2008

(54) METHODS OF USING FLT3-LIGAND IN THE TREATMENT OF FIBROSARCOMA

(75) Inventors: David H. Lynch, Bainbridge Island, WA (US); Luis Borges, Seattle, WA (US); Robert E. Miller, Everett, WA (US); Charles R. Maliszewski, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 569 days.

(21) Appl. No.: 10/241,927

(22) Filed: Sep. 11, 2002

(65) Prior Publication Data

US 2003/0113341 A1 Jun. 19, 2003

Related U.S. Application Data

(63) Continuation of application No. 09/444,027, filed on Nov. 19, 1999, now abandoned, which is a continuation-in-part of application No. 09/154,903, filed on Sep. 17, 1998, now abandoned, which is a continuation-in-part of application No. 08/725,540, filed on Oct. 3, 1996, now abandoned, which is a continuation-in-part of application No. 08/539,142, filed on Oct. 4, 1995, now abandoned.

(51) Int. Cl.
*A61K 38/19* (2006.01)
(52) U.S. Cl. .................................... 424/85.1
(58) Field of Classification Search ...................... None
See application file for complete search history.

(56) References Cited

U.S. PATENT DOCUMENTS

| | | | |
|---|---|---|---|
| 4,745,099 A | 5/1988 | Akamatsu et al. | |
| 5,013,824 A | 5/1991 | Abrams et al. | |
| 5,057,420 A | 10/1991 | Massey | |
| 5,061,620 A | 10/1991 | Tsukamoto et al. | |
| 5,114,710 A | 5/1992 | Takaku et al. | |
| 5,116,964 A | 5/1992 | Capon et al. | |
| 5,185,438 A | 2/1993 | Lemischka | |
| 5,192,553 A | 3/1993 | Boyse et al. | |
| 5,199,942 A | 4/1993 | Gillis | |
| 5,270,458 A | 12/1993 | Lemischka | |
| 5,283,354 A | 2/1994 | Lemischka | |
| 5,326,558 A | 7/1994 | Turner et al. | |
| 5,367,057 A | 11/1994 | Lemischka | |
| 5,397,706 A | 3/1995 | Correa et al. | |
| 5,399,493 A | 3/1995 | Emerson et al. | |
| 5,437,994 A | 8/1995 | Emerson et al. | |
| 5,453,357 A | 9/1995 | Hogan | |
| 5,459,069 A | 10/1995 | Palsson et al. | |
| 5,525,708 A | 6/1996 | Nocka et al. | |
| 5,548,065 A | 8/1996 | Lemischka | |
| 5,554,512 A | 9/1996 | Lyman et al. | |
| 5,626,862 A * | 5/1997 | Brem et al. | ............. 424/426 |
| 5,627,025 A | 5/1997 | Steinman et al. | |
| 5,635,388 A | 6/1997 | Bennett et al. | |
| 5,843,423 A | 12/1998 | Lyman et al. | |
| 6,017,544 A * | 1/2000 | Srivastava | ............. 424/277.1 |

FOREIGN PATENT DOCUMENTS

| | | |
|---|---|---|
| CA | 2163105 | 5/1994 |
| EP | 0 563 485 A1 | 3/1992 |
| EP | 0 627 487 A2 | 5/1994 |
| WO | WO 92/18615 | 10/1992 |
| WO | WO 93/08268 | 4/1993 |
| WO | WO 93/20186 | 10/1993 |
| WO | WO 94/26891 | 11/1994 |
| WO | WO 94/28391 | 12/1994 |
| WO | WO 95/00554 | 1/1995 |
| WO | WO 96/00779 | 1/1996 |

OTHER PUBLICATIONS

Skolnick et al., Trends in Biotech., 18(1):34 39, 2000.*
Stanley, E. R. et al., "CSF-1-A Mononuclear Phagocyte Lineage-Specific Hemopoietic Growth Factor," *J. Cell. Bio.* 21:151-159, 1983.
Y. Yarden and A. Ullrich, "Growth Factor Receptor Tyrosine Kinases," *Ann. Rev. Biochem.* 57:443-478, 1988.
J. G. Flanagan and P..Leder, "The *kit* Ligand: A Cell Surface Molecule Altered in Steel Mutant Fibroblasts," *Cell* 63:185-194, 1990.
D. Cadena and G. Gill, "Receptor tyrosine kinases," *FASEB* 6:2332-2337, 1992.
Matthews, W. et al., "A Receptor Tyrosine Kinase Specific to Hematopoietic Stem and Progenitor Cell-Enriched Populations," *Cell* 65:1143-1152, 1991.
Lyman, S. D. et al., "Characterization of the protein encoded by the flt3 (flk2) receptor-like tyrosine kinase gene," *Oncogene* 8:815-822, 1993.
Rosnet, O. et al., "Isolation and Chromosomal Localization of a Novel FMS-like Tyrosine Kinase Gene," *Genomics* 9:380-385, 1991.
Lyman, Stewart D. et al., "Molecular Cloning of a Ligand for the flt3/flk-2 Tyrosine Kinase Receptor: A Proliferative Factor for Primitive Hematopoietic Cells," *Cell* 75:1157-1167, 1993.
Maroc, N. et al., "Biochemical characterization and analysis of the transforming potential of the FLT3/FLK2 receptor tyrosine kinase," *Oncogene* 8:909-918, 1993.
Birg, F. et al., "Expression of the *FMS/KIT*-Like Gene *FLT3* in Human Acute Leukemias of the Myeloid and Lymphoid Lineages," *Blood* 80 (10):2584-2593, 1992.
Dosil, M. et al, "Mitogenic Signalling and Substrate Specificity of the Flk2/Flt3 Receptor Tyrosine Kinase in Fibroblasts and Interleukin 3-Dependent Hematopoietic Cells," *Mol. And Cell. Biol.* 13(10):6572-6585 1993.

(Continued)

*Primary Examiner*—Phillip Gambel
(74) *Attorney, Agent, or Firm*—Sughrue Mion, PLLC; James E. Klaniecki, Esq.

(57) ABSTRACT

Methods of treating a fibrosacroma using flt-3 ligand are disclosed, as well as methods of increasing the number of dendritic cells in a patient having a fibrosarcoma.

16 Claims, No Drawings

OTHER PUBLICATIONS

Hannum, C. et al., "Ligand for FLT3/FLK2 receptor tyrosine kinase regulates growth of haematopoietic stem cells and is encoded by variant RNAs," *Nature* 368:643-648, 1994.

Broxmeyer, H. E. et al., "*Commentary*: A Rapid Proliferation Assay for Unknown Co-Stimulating Factors in Cord Blood Plasma Possibly Involved in Enhancement of In Vitro Expansion and Replating Capacity of Human Hematopoietic Stem/Progenitor Cells," *Blood Cells* 20:492-497, 1994.

de Vries, P. et al., "The Effect of the FLT3 Ligand On Purified Murine Pluripotent Hematopoietic Stem Cells," *J. of Cell. Biochem. Suppl.* 18b:177, abstract #H110, 1994.

Rossner, M. T. et al., "Fms-like Tyrosine Kinase 3 Catalytic Domain Can Transduce a Proliferative Signal in FDC-P1 Cells That is Qualitatively Similar to the Signal Delivered by c-Fms[1]," *Cell Growth & Differentiation* 5:549-555, 1994.

Small, D. et al., "STK-1, the human homolog of Flk-2/Flt-3, is selectively expressed in CD34[+] human bone marrow cells and is involved in the proliferation of early progenitor/stem cells," *Proc. Natl. Acad. Sci. USA* 91:459-463, 1994.

Zeigler, F. C. et al., "Cellular and Molecular Characterization of the Role of the FLK-2/FLT-3 Receptor Tyrosine Kinase in Hematopoietic Stem Cells," *Blood* 84(8):2422-2430, 1994.

de Vries, P. et al., "The Role of FLT3 Ligand in Early Murine Hematopoiesis," *Blood* 84(10) *Suppl.* 1:279a, abstract #1100, 1994.

de Vries, P. et al., "The Effects of Soluble FLT3 Ligand On Murine Pluripotent Hematopoietic Stem Cells," *Experimental Hematology* 22(8):724, abstract #174, 1994.

Stewart, F. M. et al., "Post-5-Fluorouracil Human Marrow: Stem Cell Characteristics and Renewal Properties After Autologous Marrow Transplantation," *Blood* 81(9):2283-2289, 1993.

Bernhard, H. et al., "Generation of Immunostimulatory Dendritic Cells from Human CD34+ Hematopoietic Progenitor Cells of the Bone Marrow and Peripheral Blood," *Cancer Res.* 55:1099-1104, 1995.

Chatterjee, M. et al., "Idiotypic antibody immunotherapy of cancer," *Cancer Immunol. Immunotherap.* 38:75-82. 1994.

Boon, T., "Toward a Genetic Analysis of Tumor Rejection Antigens," *Adv. Cancer Res.* 58:177-211, 1992.

McBride, G., "New Molecule Under Study: Flt3 Ligand May Mobilize Dendritic Cells," *J. Nat'l Cancer Inst.* 89(17):1257, 1997.

Pulendran, B. et al., "Developmental Pathways of Dendritic Cells in Vivo: Distinct Function, Phenotype, and Localization of Dendritic Cell Subsets in FLT3 Ligand-Treated Mice," *J. Immunol.* 159(5):2222-2231, 1997.

Shurin, M. et al., "FLT3 Ligand Induces the Generation of Functionally Active Dendritic Cells in Mice," *Cell. Immunol.* 179(2):174-184, 1997.

Chen, K. et al., "Antitumor Activity and Immunotherapeutic Properties of Flt3-Ligand in a Murine Breast Cancer Model," *Cancer Res.* 57(16):3511-3516, 1997.

Strobl, H. et al., "flt3 Ligand in Cooperation with Transforming Growth Factor-β1 Potentiates In Vitro Development of Langerhans-Type Dendritic Cells and Allows Single-Cell Dendritic Cell Cluster Formation Under Serum-Free Conditions," *Blood*, 90(4):1425-1434, 1997.

Juan, T. et al., "Chronic Expression of Murine flt3 Ligand in Mice Results in Increased Circulating White Blood Cell Levels and Abnormal Cellular Infiltrates Associated With Splenic Fibrosis," *Blood* 90(1):76-84, 1997.

Lynch, D. et al., "Flt3 ligand induces tumor regression and antitumor immune responses in vivo," *Nature Med.* 3(6):625-631, 1997.

Saunders, D. et al., "Dendritic Cell Development in Culture from Thymic Precursor Cells in the Absence of Granulocyte/Macrophage Colony-stimulating Factor," *J. Exp. Med.* 184:2185-2196, 1996.

Maraskovsky, E. et al., "Dramatic Increase in the Numbers of Functionally Mature Dendritic Cells in Flt3 Ligand-treated Mice: Multiple Dendritic Cell Subpopulations Identified," *J. Exp. Med.* 184:1953-1962, 1996.

E. Sprecher and Y. Becker, "Role of Langerhans cells and other dendritic cells in viral diseases," *Arch. Virol.* 132:1-28, 1993.

Broxmeyer, H. et al., "Flt3 ligand stimulates/costimulates the growth of myeloid stem/progenitor cells," *Exp. Hematol.* 23:1121-1129, 1995.

A. Porgador and E. Gilboa, "Bone Marrow-generated Dendritic Cells Pulsed with a Class I-restricted Peptide are Potent Inducers of Cytotoxic T Lymphocytes," *J. Exp. Med.* 182:255-260, 1995.

Hudak, S. et al., "FLT3/FLK2 Ligand Promotes The Growth Of Murine Stem Cells And The Expansion Of Colony-Forming Cells And Spleen Colony-Forming Units," *Blood* 85(10):2747-2755, 1995.

Muench, M. et al., "FLK-2/FLT-3 Ligand Regulates The Growth Of Early Myeloid Progenitors Isolated From Human Fetal Liver," *Blood* 85(4):963-972, 1995.

Steinman, R., "The Dendritic Cell System and Its Role in Immunogenicity," *Annu. Rev. Immunol.* 9271-296, 1991.

Macatonia, S. et al., "Primary proliferative and cytotoxic T-cell responses to HIV induced in vitro by human dendritic cells," *Immunology* 74:399-406, 1991.

Pancholi, P. et al., "Dendritic Cells Efficiently Immunoselect Mycobacterial-Reactive T Cells In Human Blood, Including Clonable Antigen-Reactive Precursors," *Immunology* 76:217-224, 1992.

Inaba, K. et al., "Dendritic Cells Pulsed With Protein Antigens In Vitro Can Prime Antigen-Specific, MHC-Restricted T Cells In Situ," *J. Exp. Med.* 172:631-640, 1990.

Bujdoso, R. et al., "Afferent Lymph Dendritic Cells: A Model For Antigen Capture And Presentation In Vivo," *Intern. Rev. Immunol.* 6:177-186, 1990.

Jaffe, R., "Review Of Human Dendritic Cells: Isolation And Culture From Precursors," *Pediatric Pathology* 13:821-837, 1993.

Bermstein, I. et al., "Isolation Of Human Hematopoietic Stem Cells," *Blood Cells* 20:15-24, 1994.

Young, J. et al., "Identification Of Dendritic Cell Colony-Forming Units Among Normal Human CD34[+] Bone Marrow Progenitors That Are Expanded By C-Kit Ligand And Yield Pure Dendritic Cell Colonies In The Presence Of Granulocyte/Macrophage Colony-Stimulating Factor And Tumor Necrosis Factor α," *J. Exp. Med.* 182:1111-1120, 1995.

Inaba, K. et al., "Dendritic Cell Progenitors Phagocytose Particulates, Including Bacillus Calmette-Guerin Organisms, And Sensitize Mice To Mycobacterial Antigens In Vivo," *J. Exp. Med.* 178:479-488, 1993.

Papayannopoulo et al., "In Vivo Effects of Flt3/Flk2 Ligand on Mobilization of Hematopoietic Progenitors in Primates and Potent Synergistic Enhancement with Granulocyte Colony-Stimulating Factor," *Blood* 90:620-629, 1997.

Lotem, J. and Sachs, L., "Control of In Vivo Differentiation of Myeloid Leukemic Cells," *Leukemia* 2(12 *Suppl.*):24S-37S, 1988.

Stewart D. Lyman et al., "Cloning of the Human Homologue of the Murine flt3 Ligand: A Growth Factor for Early Hematopoietic Progenitor Cells," *Blood* 83(10):2795-2801, 1994.

D. Hanahan, "Transgenic Mice as Probes into Complex Systems," *Science* 246:1265-1275, 1989.

Romani, N. et al., "Proliferating Dendritic Cell Progenitors in Human Blood," *J. Exp. Med.* 180:83-93, 1994.

Winton, E. F. et al., "Recombinant Human (rh) FLT3 Ligand Plus rhGM-CSF or rhG-CSF Causes a Marked CD34[+] Cell Mobilization to Blood in Rhesus Monkeys," ASH Abstract, Dec. 1996.

F. Sallusto and A. Lanzavecchia, "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factorα," *J. Exp. Med.* 179:1109-1118, 1994.

Szabolcs, P. et al, "Expansion of Immunostimulatory Dendritic Cells Among the Myeloid Progeny of Human CD34[+] Bone Marrow Precursors Cultured with c-kit Ligand, Granulocyte-Macrophage Colony-Stimulating Factor, and TNF-α'," *J. Immunl.* 154:5851-5861, 1995.

Rosnet, O. et al., "Murine *Flt3*, a gene encoding a novel tyrosine kinase receptor of the PDGFR/CSF1R family," *Oncogene* 6:1641-1650, 1991.

S. Stengelin et al., "Isolation of cDNAs for two distinct human Fc receptors by ligand affinity cloning," *EMBO J.* 7(4):1053-1059, 1988.

Debets, R. and Savelkoul, H. F. J. "Cytokine antagonists and their potential therapeutic use," *Immunol. Today* 15(10):455-458, 1994.

Small et al., "STK-1 is Expressed in a Subpopulation of Human Bone Marrow Enriched for CD34+ Progenitor/Stem Cells and in a Number of Leukemic Cell Lines," *Blood 80*, 296a; Abstract No. 1175, 1992.

Reid, D. L. et al., "Interactions Of Tumor Necrosis Factor With Granulocyte-Macrophage Colony-Stimulating Factor And Other Cytokines In The Regulation Of Dendritic Cell Growth In Vitro From Early Bipotent CD34+ Progenitors In Human Bone Marrow," *J. of Immunol.* 149(8):2681-2688, 1992.

Thomson, A. W. et al., "Microchimerism, Dendritic Cell Progenitors and Transplantation Tolerance," *Stem Cells* 13:622-639, 1995.

Lyman, S. D. and Jacobsen, S. E. W., "c-kit Ligand and Flt-3 Ligand: Stem/Progenitor Cell Factors With Overlapping Yet Distinct Activities," *Blood* 91(4): 1101-1134, 1998.

Ray, R. J. et al., "Flt3 ligand supports the differentiation of early B cell progenitors in the presence of IL-11 and IL-7," Manuscript, Feb. 20, 1996.

Chklovskaia, E. et al., "Increased Production of FLT3 Ligand in Leukemia Patients With Chemotherapy-Induced Bone Marrow Suppression," 1996 EHA Abstract Form, Second Meeting of the European Haematology Association, May 29-Jun. 1, 1996.

Wodnar-Filipowicz, A. et al., "Tyrosine kinase receptors and their ligands in aplastic anemia," Manuscript, Feb. 20, 1996.

Hsu, F. et al., "Antigen-Pulsed Dendritic Cells in the Treatment of Patients with B-cell Lymphoma," Abstract # C1-314, Keystone Conference, Taos, NM, Mar. 1995.

Drexhage, H. A., "A Defective Maturation and Function of Dendritic Cells in Type 1 Diabetics," Abstract # C1-204, Keystone Conference, Taos, NM, Mar. 1995.

Fisch, P. et al., "Ex Vivo Generation of Functionally Active Antigen Presenting Cells From Peripheral Blood CD34+ Hematopoietic Progenitor Cells in Cancer Patients," Abstract # C1-311, Keystone Conference, Taos, NM, Mar. 1995.

Mayordomo, J. et al., "Bone Marrow-Derived Dendritic Cells Serve as Potent Adjuvants for Peptide-Based Antitumor Vaccines," Abstract # C1-213, Keystone Conference, Taos, NM, Mar. 1995.

Lenz, P. et al., "MHC Class I+/II Dendritic Cells Sensitize for Transplantation Immunity," Abstract # C1-318, Keystone Conference, Taos, NM, Mar. 1995.

Ye, Z. et al., "Evaluation of Dendritic Cells in Allogeneic Marrow Grafts," Abstract # C1-130, Keystone Conference, Taos, NM, Mar. 1995.

Thomson, A. W. et al., "Growth of Donor-Derived Dendritic Cells From the Bone Marrow of Murine Liver Allograft Recipients in Response to Granulocyte/Macrophage Colony-Stimulating Factor," Abstract # C1-125, Keystone Conference, Taos, NM, Mar. 1995.

Whalen, R. G. et al., "DNA-Mediated Immunization to the Hepatitis B Surface Antigen: Potential Involvement of Interstitial Dendritic Cells," Abstract # C1-128, Keystone Conference, Taos, NM, Mar. 1995.

Alters, S. et al., Characterization and Gene Modification of Dendritic Cells to be Used for Antigen Presentation, Abstract # C1-302, Keystone Conference, Taos, NM, Mar. 1995.

\* cited by examiner

METHODS OF USING FLT3-LIGAND IN THE TREATMENT OF FIBROSARCOMA

RELATED APPLICATIONS

This application is a continuation of U.S. application Ser. No. 09/444,027, filed Nov. 19, 1999, now abandoned, which is a continuation-in-part of U.S. application Ser. No. 09/154,903, filed Sep. 17, 1998, now abandoned, which is a continuation-in-part of U.S. application Ser. No. 08/725,540, filed Oct. 3, 1996, now abandoned, which is continuation-in-part of U.S. application Ser. No. 08/539,142, filed Oct. 4, 1995, now abandoned.

FIELD OF THE INVENTION

The present invention relates to a dendritic cell stimulatory factor, to methods of enhancing an immune response in vivo, methods of expanding dendritic cells ex vivo, and to preparations of purified dendritic cells, and to dendritic cell populations useful in the manipulation of T cell-mediated and B-cell mediated immune responses.

BACKGROUND OF THE INVENTION

The objective of vaccination is to provide effective immunity by establishing adequate levels of antibody and a primed population of cells that can rapidly expand on renewed contact with antigen. The first contact with antigen during vaccination must not be injurious to the recipient and thus usually consists of pathogenically-deficient antigen.

A frequent difficulty with active immunization protocols is that the vaccine antigen does not possess sufficient immunogenicity to promote a strong immune response, and therefore a sufficient level of protection against subsequent challenge by the same antigen. In addition, certain antigens may elicit only weak cell-mediated or antibody responses. For many antigens, both a strong humoral response and a strong cell-mediated response is desirable.

For decades, researchers have experimented with diverse compounds to increase the immunogenicity of vaccines. Immunopotentiators, also known as adjuvants, of vaccines are compositions of matter that facilitate a strong immune response to a vaccine. In addition, the relatively weak immunogenicity of certain novel recombinant antigens has required adjuvants to be more potent. Vaccine adjuvants have different modes of action, affecting the immune response both quantitatively and qualitatively. Such modes of action can be by mobilizing T cells, acting as depots and altering lymphocyte circulation so that these cells remain localized in draining lymph nodes. They may also serve to focus antigen at the site of immunization, thereby allowing antigen specific T cells and B cells to interact more efficiently with antigen-presenting cells. They may also stimulate proliferation and differentiation of T cells and have effects on B cells, such as enhancing the production of different Ig isotypes. Further, adjuvants may stimulate and affect the behavior of antigen-presenting cells, particularly dendritic cells and macrophages, rendering them more effective for presenting antigen to T cells and B cells.

Dendritic cells are a rare and heterogeneous cell population with distinctive morphology and a widespread tissue distribution. A discussion of the dendritic cell system and its role in immunogenicity is provided by Steinman, R. M., *Annu. Rev. Immunol.*, 9:271-296 (1991), incorporated herein by reference. Dendritic cells display an unusual cell surface phenotype and can be characterized by the presence of the cell surface markers CD1, CD4, CD86, CD11c, DEC-205, CD40 or HLA-DR, and the absence of CD14 and other lineage markers. Dendritic cells have a high capacity for sensitizing MHC-restricted T cells and provide an effective pathway for presenting antigens to T cells in situ, both self-antigens during T cell development and foreign antigens during immunity. Thus, there is growing interest in using dendritic cells ex vivo as tumor or infectious disease vaccine adjuvants. See, for example, Romani, et al., *J. Exp. Med.*, 180:83 (1994). The use of dendritic cells as immunostimulatory agents has been limited due to the low frequency of dendritic cells in peripheral blood, the limited accessibility to lymphoid organs and the dendritic cells' terminal state of differentiation. Dendritic cells originate from CD34+ bone marrow progenitors, and the proliferation and maturation of dendritic cells can be enhanced by the cytokines GM-CSF (sargramostim, Leukine®, Immunex Corporation, Seattle, Wash.), TNF-α, c-kit ligand (also known as stem cell factor (SCF), steel factor (SF), or mast cell growth factor (MGF)) and interleukin-4. Therefore, an agent that stimulated the generation of large numbers of functionally mature dendritic cells in vivo or in vitro would be of wide importance.

SUMMARY OF THE INVENTION

Flt3-ligand ("flt3-ligand," "flt3-L," "Flt3-L") is known to affect hematopoietic stem and progenitor cells. It was surprisingly found that flt3-ligand can also potently stimulate the generation of downstream or intermediate, cells such as myeloid precursor cells, monocytic cells, macrophages, B cells, and dendritic cells from CD34+ bone marrow progenitors and stem cells. The present invention pertains to a method of mobilizing dendritic cells in vivo, expanding dendritic cells ex vivo and to preparations of dendritic cells. The preparation of purified dendritic cells according to the invention would potentially find use as vaccine adjuvants. Also included within the embodiments of the invention is a method of preparing antigen-specific T cells using the dendritic cells mobilized with flt3-ligand.

The invention provides for the use of an effective amount of flt3-ligand to increase or mobilize the numbers of intermediate cells in vivo, for example, in the patient's peripheral blood or spleen. While the invention relates to the generation of large numbers of such downstream and intermediate cells (e.g., myeloid cells, monocytic cells and macrophages) from CD34+ cells using flt3-ligand, the focus is particularly on dendritic cells. By increasing the quantity of the patient's dendritic cells, such cells may themselves be used to present antigen to T cells. For example, the antigen may be one that already exists within the patient, such as a tumor antigen, or a bacterial or viral antigen. Flt3-L may be used, therefore, to increase the numbers of dendritic cells in vivo to boost a patient's immune response against existing antigens. The invention further provides for using combination therapy to enhance a patient's immune response. Such combination therapy includes administering flt3-ligand and one or more therapeutic reagents in amounts sufficiently effective to upregulate the patient's immune response. Alternatively, flt3-ligand may be administered prior to, concurrently with or subsequent to administration of an antigen to a patient for immunization purposes. Thus, as a vaccine adjuvant, flt3-ligand can generate large quantities of dendritic cells in vivo to more effectively present the antigen. The overall response is a stronger and improved immune response and more effective immunization to the antigen.

The invention also provides a method of generating large quantities of dendritic cells ex vivo. Following collection of the patient's CD34+ hematopoietic progenitors and stem cells, flt3-ligand can be used to expand such cells in vitro (also known as ex vivo expansion) and to drive such CD34+ cells to differentiate into dendritic cells of the lymphoid or myeloid lineage. The resulting collection of dendritic cells can be administered to a patient to provide a stronger and improved immune response to an antigen. Alternatively, the resulting dendritic cells find use as a vaccine adjuvant and can be administered prior to, concurrently with or subsequent to antigen administration.

The invention also provides a method of generating large quantities of antigen-presenting dendritic cells ex vivo. Following collection of the patient's CD34+ hematopoietic progenitors and stem cells, flt3-ligand can be used to expand such cells in vitro and to drive such CD34+ cells to differentiate into dendritic cells. The resulting collection of dendritic cells is exposed to an antigen and allowed to process and present the antigen in vitro (this procedure is sometimes referred to in the art as "antigen-pulsing"). An alternate method for preparing dendritic cells that present antigen is to transfect the dendritic cells with a gene encoding an antigen-specific polypeptide. Once the dendritic cells express the antigen, the antigen-presenting dendritic cells can be administered to a patient.

The invention also provides for the ex vivo preparation of antigen-specific T cells. Following the procedures described above for preparing large numbers of antigen-presenting dendritic cells ex vivo, the collected antigen-presenting dendritic cells are used to generate antigen-specific T cells from naive T cells that have been collected from a patient. After the antigen has been adequately presented to the T cells generated, the antigen-specific T cells can be administered to the patient.

The invention also provides a method of augmenting an immune response in a patient that has an infectious disease wherein the method comprises the step of administering an amount of flt3-ligand sufficient to increase the patient's number of dendritic cells. Embodiments of methods for augmenting an immune response include administering flt3-ligand in combination therapies with additional active compounds, including but not limited to CD40 binding proteins, 4-1BB-L, antibodies to 4-1BB, interferon alpha, RANKL, a CD30 ligand antagonist, and combinations thereof.

The invention also provides a method of augmenting an immune response in a patient that has a cancerous or neoplastic disease wherein the method comprises the step of administering an amount of flt3-ligand sufficient to increase the patient's number of dendritic cells. Embodiments of methods for augmenting an immune response include administering flt3-ligand in combination therapies with additional active compounds, including but not limited to CD40 binding proteins, 4-1BB-L, antibodies to 4-1BB, interferon alpha, RANKL, a CD30 ligand antagonist, and combinations thereof. Such method provides a means to enhance the patient's tumor-specific immune response.

A method for enhancing a patient's autoimmune tolerance wherein the method comprises the step of administering an amount of flt3-ligand sufficient to increase the patient's number of dendritic cells. Further included are methods for promoting survival of grafts and transplanted tissues and organs.

The methods of the invention can further comprise the use of an effective amount of a cytokine in sequential or concurrent combination with flt3-ligand. Such cytokines include, but are not limited to, interleukins ("ILs") IL-3 and IL-4, a colony stimulating factor ("CSF") selected from the group consisting of granulocyte macrophage colony stimulating factor ("GM-CSF") or GM-CSF/IL-3 fusions, or other cytokines such as TNF-α, CD40 binding proteins (e.g. CD40-L), 4-1BB antagonists (e.g., antibodies immunoreactive with 4-1BB and 4-1BB-L), interferon alpha, RANKL, CD30 ligand antagonists (e.g., CD30 ligand monoclonal antibodies and soluble CD30-Fc fusion polypeptides), and c-kit ligand.

The invention further includes a dendritic cell expansion medium comprising cell growth medium, autologous serum, and flt3-ligand alone or in combination with a cytokine from the group listed above.

DETAILED DESCRIPTION OF THE INVENTION

The invention is directed to the use of flt3-ligand to generate large numbers of intermediate cell types from CD34+ hematopoietic progenitor cells and stem cells. Such intermediate cell types include myeloid cells, monocytic cells, macrophages and dendritic cells. The large numbers of these intermediate cell types are not naturally found in vivo and can be generated by administering flt3-ligand. Such enhancement in overall cell number can augment the immune response to antigen in the host. Another embodiment of the invention is the isolation and use of such intermediate cell types as antigen-presenting cells or the use as vaccine adjuvants. The invention, while particularly focused on the embodiment concerning dendritic cells, is also applicable to myeloid, monocytic and macrophage cell types.

As used herein, the term "flt3-ligand" refers to a genus of polypeptides that are described in U.S. Pat. No. 5,554,512, EP 0627487 A2 and in WO 94/28391, both incorporated herein by reference. A human flt3-ligand cDNA was deposited with the American Type Culture Collection, Rockville, Md., USA (ATCC) on Aug. 6, 1993 and assigned accession number ATCC 69382. The deposit was made under the terms of the Budapest Treaty. Flt3-L can be made according to the methods described in the documents cited above.

As described in U.S. Pat. No. 5,554,512 at column 5, line 15, the term "flt3-L" encompasses proteins having the amino acid sequence 1 to 235 of SEQ ID NO:2, as well as those proteins having a high degree of similarity or a high degree of identity with the amino acid sequence 1 to 235 of SEQ ID NO:2, and which proteins are biologically active and bind the flt3 receptor. In addition, the term refers to biologically active gene products of the DNA of SEQ ID NO:1. Further encompassed by the term "flt3-L" are the membrane-bound proteins (which include an intracellular region, a membrane region, and an extracellular region), and soluble or truncated proteins which comprise primarily the extracellular portion of the protein, retain biological activity and are capable of being secreted. Specific examples of such soluble proteins are those comprising the sequence of amino acids 28-160 of SEQ ID NO:2.

A "flt3-L variant" as referred to herein, means a polypeptide substantially homologous to native flt3-L, but which has an amino acid sequence different from that of native flt3-L (human, murine or other mammalian species) because of one or more deletions, insertions or substitutions. The variant amino acid sequence preferably is at least 80% identical to a native flt3-L amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring flt3-L variants are also encompassed by the invention. Examples of such variants are proteins that result from alternate mRNA splicing events or from proteolytic cleavage of the flt3-L protein, wherein the flt3-L binding property is retained. Alternate splicing of mRNA may yield a truncated but biologically active flt3-L protein, such as a naturally occurring soluble form of the protein, for example. Variations attributable to proteolysis include, for example, differences in the N- or C-termini upon expression in different types of host cells, due to proteolytic removal of one or more terminal amino acids from the flt3-L protein (generally from 1-5 terminal amino acids).

As described in U.S. Pat. No. 5,554,512 at column 8, line 7, an aspect of the invention is soluble flt3-L polypeptides. Soluble flt3-L polypeptides comprise all or part of the extracellular domain of a native flt3-L but lack the transmembrane region that would cause retention of the polypeptide on a cell membrane. Soluble flt3-L polypeptides advantageously comprise the native (or a heterologous) signal peptide when initially synthesized to promote secretion, but the signal peptide is cleaved upon secretion of flt3-L from the cell. Soluble flt3-L polypeptides encompassed by the invention retain the ability to bind the flt3 receptor. Indeed, soluble flt3-L may also include part of the transmembrane region or part of the cytoplasmic domain or other sequences, provided that the soluble flt3-L protein can be secreted.

Soluble flt3-L may be identified (and distinguished from its non-soluble membrane-bound counterparts) by separating intact cells which express the desired protein from the culture medium, e.g., by centrifugation, and assaying the medium (supernatant) for the presence of the desired protein. The presence of flt3-L in the medium indicates that the protein was secreted from the cells and thus is a soluble form of the desired protein.

Soluble forms of flt3-L possess many advantages over the native bound flt3-L protein. Purification of the proteins from recombinant host cells is feasible, since the soluble proteins are secreted from the cells. Further, soluble proteins are generally more suitable for intravenous administration.

Examples of soluble flt3-L polypeptides include those comprising a substantial portion of the extracellular domain of a native flt3-L protein. Such soluble mammalian flt3-L proteins comprise amino acids 28 through 182 of SEQ ID NO:2. In addition, truncated soluble flt3-L proteins comprising less than the entire extracellular domain are included in the invention. Such truncated soluble proteins are represented by the sequence comprising amino acids 28-160 of SEQ ID NO:2. When initially expressed within a host cell, soluble flt3-L may additionally comprise one of the heterologous signal peptides described below that is functional within the host cells employed. Alternatively, the protein may comprise the native signal peptide, such that the mammalian flt3-L comprises 1 through 182 of SEQ ID NO:2. Isolated DNA sequences encoding soluble flt3-L proteins are encompassed by the invention.

The term "IL-3" refers to a genus of interleukin-3 polypeptides as described in U.S. Pat. No. 5,108,910, incorporated herein by reference. Such polypeptides include analogs that have amino acid sequences that are substantially similar to the native human interleukin-3 amino acid sequences disclosed, for example, in EP publ. Nos. 275,598 and 282,185, each incorporated herein by reference. The term "IL-3" also includes analogs and alleles of IL-3 molecules that exhibit at least some of the biological activity in common with native human IL-3. Exemplary analogs of IL-3 are disclosed in EP Publ. No. 282,185. Other forms of IL-3 include human IL-3[Pro$^8$Asp$^{15}$Asp$^{70}$], human IL-3 [Ser$^8$Asp$^{15}$Asp$^{70}$] and human IL-3[Ser$^8$]. A DNA sequence encoding human IL-3 protein suitable for use in the invention is publicly available from the American Type Culture Collection (ATCC) under accession number ATCC 67747. The nomenclature used herein with respect to amino acid sequences in brackets designates which amino acids differ from the native human form. For example, human IL-3 [Ser$^8$Asp$^{15}$Asp$^{70}$] refers to a human IL-3 protein in which amino acid 8 has been changed to a serine residue, amino acid 15 has been changed to an aspartic acid residue and the amino acid 70 has been changed to an aspartic acid residue.

The term "IL-4" refers to a polypeptide as described in Mosley et al., *Cell* 59:335 (1989), Idzerda et al., *J. Exp. Med.* 171:861 (1990) and Galizzi et al., *Intl. Immunol.* 2:669 (1990), each of which is incorporated herein by reference. Such IL-4 polypeptide includes analogs that have an amino acid sequence that is substantially similar to the native human IL-4 amino acid sequences described in Mosley et al., Idzerda et al., and Galizzi et al. and which are biologically active in that they are capable of binding to a IL-4 receptor, transducing a biological signal initiated by binding IL-4 receptor, or cross-reacting with anti-IL-4 antibodies. The term "IL-4" also includes analogs of native human IL-4 molecules sufficient to retain biological activity of native human IL-4.

As used herein, "GM-CSF" refers to a genus of proteins as described in U.S. Pat. Nos. 5,108,910, and 5,229,496 each of which is incorporated herein by reference. Such proteins include analogs that have an amino acid sequence that is substantially similar to native human GM-CSF amino acid sequences (e.g., as publicly available ATCC 53157 or ATCC 39900), and which are biologically active in that they are capable of binding to a GM-CSF receptor, transducing a biological signal initiated by binding GM-CSF receptor, or cross-reacting with anti-GM-CSF antibodies. Amino acid sequences are disclosed, for example in Anderson, et al., *Proc. Natl. Acad. Sci., USA* 82:6250 (1985). Commercially available GM-CSF (sargramostim, Leukine®) is obtainable from Immunex Corp., Seattle, Wash.). The term "GM-CSF" also includes analogs of the native human GM-CSF molecules described in U.S. Pat. Nos. 5,108,910, and 5,229,496 sufficient to retain biological activity of native human GM-CSF. Exemplary analogs of GM-CSF include, for example, those described in EP Publ. No. 212914 and WO 89/03881, each of which is incorporated herein by reference. Other analogs of GM-CSF also may be used to construct fusion proteins with IL-3. A DNA sequence encoding a particularly preferred GM-CSF protein having potential glycosylation sites removed is publicly available from the ATCC under accession numbers ATCC 67231.

The term "GM-CSF/IL-3 fusion protein" means a C-terminal to N-terminal fusion of GM-CSF and IL-3. The fusion proteins are known and are described in U.S. Pat. Nos. 5,199,942, 5,108,910 and 5,073,627, each of which is incorporated herein by reference. A preferred fusion protein is PIXY321 as described in U.S. Pat. No. 5,199,942.

The term "c-kit ligand" also known as Mast Cell Growth Factor (MGF), Steel Factor or Stem Cell Factor (SCF), refers to a polypeptide described in EP 423,980, which is incorporated herein by reference, and that claims priority from U.S. patent application Ser. No. 589,701, filed Oct. 1, 1990. Such c-kit ligand polypeptide includes analogs that have an amino acid sequence that is substantially similar to the native human c-kit ligand amino acid sequences described in EP 423,980 and which are biologically active in that they are capable of binding to a c-kit receptor, transducing a biological signal initiated by binding c-kit receptor, or cross-reacting with anti-c-kit ligand antibodies. The term "c-kit ligand" also includes analogs of native human c-kit ligand molecules sufficient to retain biological activity of native human c-kit ligand.

The term "CD40 binding protein" refers to polypeptides that bind CD40, including but not limited to CD40-L and antibodies immunoreactive with CD40, as described in PCT publications WO 93/08207 and WO 96/40918 each of which is incorporated herein by reference. Such CD40 binding proteins include analogs that have an amino acid sequence that is substantially similar to the native human CD40-L amino acid sequences described in the PCT publications, and which are biologically active in that they are capable of binding to CD40, transducing a biological signal initiated by binding CD40, or cross-reacting with anti-CD40 antibodies. The term CD40 binding proteins also includes analogs of native human CD40-L and antibodies reactive with CD40 that are sufficiently homologous to native molecules so as to retain biological activity of native CD40 binding proteins.

The terms "4-1BB-L" and "antibody to 4-1BB" refer to molecules that are described in U.S. Pat. No. 5,674,704 and Alderson et al. *Eur. J. Immunol.* 24:2219-2227, 1994, which are incorporated herein by reference. 4-1BB-L includes analogs that have an amino acid sequence that is substantially similar to the native 4-1BB-L amino acid sequence described in the above mentioned publication and which are biologically active in that they are capable of binding to 4-1BB or transducing a biological signal initiated by binding 4-1BB, such as inducing a proliferative response in stimulated primary T cells. The terms 4-1BB-L and antibodies to 4-1BB also includes analogs of native 4-1BB-L and analogs of antibodies reactive with 4-1BB that are sufficiently homologous to the native compounds so as to retain biological activity of 4-1BB-L and the described antibodies.

The term "interferon alpha" refers to naturally occurring forms of interferon alpha (leukocyte interferon) as isolated from cells, cell lines, tissue, and other sources, as well as recombinant forms, consensus forms, analogs, and variant forms that exhibit interferon alpha biological activity. Hybrid "interferon alpha A/D," also called "Universal Type I Interferon," has been described by Fisher et al., *Biochem Biophys. Res. Commun.* 119(1):108 (1984), incorporated herein by reference. Interferon alpha polypeptides have been described in, inter alia, Pestka et al., *Ann. Rev. Biochem.* 56:727 (1987), Goeddel et al., *Nature* 290:20 (1980), Petska et al., in *Human Cytokines,* Blackwell Scientific Publications 1-16 (1992), Petska, *Semin. Oncol.* 24(3):S9-4 (197), U.S. Pat. No. 4,414,150, and WO 96/11953, all of which are incorporated herein by reference.

The term "CD30 ligand antagonist" refers to any molecule that interferes with the binding between CD30 ligand and the CD30 receptor. CD30 ligand is described, inter alia, in U.S. Pat. No. 5,480,981 which is incorporated herein by reference. CD30 ligand antagonists include, but are not limited to, CD30 ligand antibodies (including CD30 ligand monoclonal antibodies) and soluble CD30 polypeptides and analogs thereof (including soluble CD30-Fc fusion polypeptides). CD30 ligand antagonists may also be antisense nucleic acids, ribozymes, muteins, aptamers, and small molecules that interfere with the CD30-CD30 ligand interaction.

"RANK ligand" ("RANKL") polypeptides are described in, inter alia, WO 98/28426; "TRAIL" polypeptides are described in, inter alia, U.S. Pat. No. 5,763,223; "Tek" (also called Tie2, ork) polypeptides are described in, inter alia, U.S. Pat. No. 5,447,860. These publications are incorporated herein by reference.

The term "adjuvant" refers to a substance that enhances, augments or potentiates the host's immune response to a vaccine antigen.

The term "antagonist" includes various classes of molecules that are capable of interfering with a specified biological interaction and/or activity. Antagonists include, but are not limited to, antibodies, soluble forms of a target polypeptide, antisense nucleic acids, ribozymes, muteins, aptamers, and small molecules.

The procedure for "ex vivo expansion" of hematopoietic stem and progenitor cells is described in U.S. Pat. No. 5,199,942, incorporated herein by reference. Briefly, the term means a method comprising: (1) collecting $CD34^+$ hematopoietic stem and progenitor cells from a patient from peripheral blood harvest or bone marrow explants; and (2) expanding such cells ex vivo . In addition to the cellular growth factors described in U.S. Pat. No. 5,199,942, other factors such as flt3-ligand, IL-1, IL-3, c-kit ligand, can be used.

The term "immunogenicity" means relative effectiveness of an immunogen or antigen to induce an immune response.

The term "substantially similar" means a variant amino acid sequence preferably that is at least 80% identical to a native amino acid sequence, most preferably at least 90% identical. Percent identity may be determined by visual inspection. Percent identity may be determined using the alignment method of Needleman and Wunsch (J. Mol. Biol. 48:443, 1970) as revised by Smith and Waterman (Adv. Appl. Math 2:482, 1981). Preferably, percent identity is determined by using a computer program, for example, the GAP computer program version 10.x available from the Genetics Computer Group (GCG; Madison, Wis., see also Devereux et al., *Nucl. Acids Res.* 12:387, 1984). The preferred default parameters for the GAP program include: (1) a comparison matrix containing a value of 1 for identities and 0 for non-identities for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353-358, 1979 for amino acids; (2) a penalty of 30 (amino acids) or 50 (nucleotides) for each gap and an additional 1 (amino acids)

or 3 (nucleotides) penalty for each symbol in each gap; (3) no penalty for end gaps; and (4) no maximum penalty for long gaps.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events or from proteolytic cleavage of the native protein, wherein the native biological property is retained.

As used herein, "vaccine" means an organism or material that contains an antigen in an innocuous form. The vaccine is designed to trigger an immunoprotective response. The vaccine may be recombinant or non-recombinant. When inoculated into a non-immune host, the vaccine will provoke active immunity to the organism or material, but will not cause disease. Vaccines may take the form, for example, of a toxoid, which is defined as a toxin that has been detoxified but that still retains its major immunogenic determinants; or a killed organism, such as typhoid, cholera and poliomyelitis; or attenuated organisms, that are the live, but non-virulent, forms of pathogens, or it may be antigen encoded by such organism, or it may be a live tumor cell or an antigen present on a tumor cell.

A variety of cell selection techniques are known for identifying and separating $CD34^+$ hematopoietic stem or progenitor cells from a population of cells. Methods and materials for identifying and selecting such cell types are known. For example, monoclonal antibodies can be used to bind to a marker protein or surface antigen protein found on stem or progenitor cells. Such markers or cell surface antigens for hematopoietic stem cells include CD34 and Thy-1. In one method, antibodies are fixed to a surface, for example, glass beads, and contacted with a mixture of cells suspected of containing stem cells. This permits the antibodies to bind and secure the stem cells to the glass beads. Alternatively, the antibodies can be incubated with the cell mixture and the resulting combination contacted with a surface having an affinity for the antibody-cell complex. Undesired cells and cell matter are removed providing a relatively pure population of stem cells. Stem or progenitor cells having the CD34 marker constitute only about 1% to 3% of the mononuclear cells in the bone marrow. The amount of $CD34^+$ stem or progenitor cells in the peripheral blood is approximately 10- to 100-fold less than in bone marrow.

With regard to the particular aspects of the invention, choosing suitable stem or progenitor cell selection means will depend on the desired phenotype of the cell to be isolated. Hematopoietic stem cells are selectable by virtue of their physical characteristics, such as expressing the membrane-bound flt3 receptor, or having the following cellular markers: CD34 or Thy-1. Monoclonal antibodies that recognize any of these antigens have been described in U.S. Pat. No. 4,714,680 (anti-My-10) incorporated herein by reference, anti-CD34 is commercially available from Becton Dickinson, Franklin Lakes, N.J.), and anti-Thy-1 monoclonal antibodies can be readily generated using the methods described by Dalchau et al., *J. Exp. Med.* 149:576 (1979), incorporated herein by reference. A flt3 receptor binding protein also may be used, such as anti-flt3 monoclonal antibodies or the flt3-ligand. The cell binding protein is brought into contact with the collected cell mixture and the combination is allowed to incubate for a period of time sufficient to permit the binding of the desired cell to the cell binding protein.

An alternative means of selecting the quiescent stem cells is to induce cell death in the dividing, more lineage-committed, cell types using an antimetabolite such as 5-fluorouracil (5-FU) or an alkylating agent such as 4-hydroxycyclophosphamide (4-HC). The non-quiescent cells are stimulated to proliferate and differentiate by the addition of growth factors that have little or no effect on the stem cells, causing the non-stem cells to proliferate and differentiate and making them more vulnerable to the cytotoxic effects of 5-FU or 4-HC. See Berardi et al., *Science,* 267:104 (1995), which is incorporated herein by reference.

Isolation of the hematopoietic stem or progenitor cells can be performed by using, for example, affinity chromatography, antibody-coated magnetic beads, or antibodies fixed to a solid matrix, such as glass beads, flasks, etc. Antibodies that recognize a stem or progenitor cell surface marker can be fused or conjugated to other chemical moieties such as biotin—which can be removed with an avidin or a streptavidin moiety secured to a solid support; fluorochromes useful in fluorescence activated cell sorting (FACS), or the like. Preferably, isolation is accomplished by an immunoaffinity column. Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. Typical substrates include avidin and streptavidin, while other conventional substrates can be used. The substrate should, either by its own properties, or by the addition of a chemical moiety, display high-affinity for a moiety found on the cell-binding protein such as a monoclonal antibody. The monoclonal antibodies recognize a cell surface antigen on the cells to be separated, and are typically further modified to present a biotin moiety. It is well-known that biotin has a high affinity for avidin, and the affinity of these substances thereby removably secures the monoclonal antibody to the surface of the packed bed. Such columns are well known in the art, see Berenson, et al., *J. Cell Biochem.,* 10D:239 (1986). The column is washed with a PBS solution to remove unbound material. Target cells can be released from the beads using conventional methods. Immunoaffinity columns of the type described above that utilize biotinylated anti-CD34 monoclonal antibodies secured to an avidin-coated packed bed are described for example, in PCT Publ. No. WO 93/08268. A variation of this method utilizes cell binding proteins, such as the monoclonal antibodies or flt3-ligand as described above, removably-secured to a fixed surface in the isolating means. The bound cell binding protein then is contacted with the collected cell mixture and allowed to incubate for a period of time sufficient to permit isolation of the desired cells.

Alternatively, the monoclonal antibodies that recognize the cell surface antigens can be labeled with a fluorescent label, e.g., chromophore or fluorophore, and separated by cell sorting according to the presence of absence or the amount of labeled product.

The collected $CD34^+$ cells are then exposed to either flt3-ligand alone or flt3-ligand in concurrent or sequential combination with one or more of the following cytokines: GM-CSF, TNF-α, IL-3, IL-4, c-kit-ligand, CD40-L, 4-1BB-L or GM-CSF/IL-3 fusion proteins. CD34+ cells then are allowed to differentiate and commit to cells of the dendritic lineage. The dendritic cells are collected and can either be (a) administered to a patient in order to augment the immune system and T-cell mediated or B-cell mediated immune responses to antigen, (b) exposed to an antigen prior to administration of the dendritic cells into a patient, (c) transfected with a gene encoding an antigen-specific polypeptide or (d) exposed to an antigen and then allowed to process and present the antigen, ex vivo, to T-cells collected from the patient followed by administration of the antigen-specific T-cells to the patient.

More specifically, the invention provides for the use of an effective amount of flt3-ligand to increase or mobilize dendritic cells in vivo, for example, in the patient's peripheral blood or spleen. By increasing the quantity of the patient's dendritic cells, such cells may themselves be used to present antigen to T cells. For example, the antigen may be one that already exists within the patient, such as a tumor antigen, or a bacterial or viral antigen. Flt3-L may be used, therefore, to boost the patient's lymphocyte-mediated (e.g., T cell and B cell mediated) or myeloid-mediated immune response to the already present antigens thus potentially enabling a more effective antigen-presentation to the patient's T cells.

Further, flt3-L may be used in combination therapies with one or more additional agents to enhance an immune response against tumor, viral or bacterial antigens. For example, CD40 binding proteins, which enhance the ability of dendritic cells to process and present antigens to effector T cells can be administered in combination with flt3-L to dramatically enhance an immune response. Such immune responses can include responses against viral or bacterial antigens that are responsible for infectious diseases and immune responses to tumor antigens. As described in Example 4, a surprising synergy between a CD40 binding protein and flt3-L has been discovered for their combined ability to enhance anti-tumor responses. Representative CD40 binding proteins useful in combination therapy with flt3-L include CD40-L and antibodies immunoreactive with CD40 which are described in PCT publications WO 93/08207 and WO 96/40918.

Additionally, 4-1BB-L and antibodies reactive with 4-1BB, both of which are T-cell co-activation factors, can be administered in combination with flt3-L to dramatically enhance immune responses. 4-1BB-L and antibodies reactive with 4-1BB can be used in combination therapies to enhance immune responses to viral antigens and bacterial antigens responsible for infectious diseases and to enhance immune responses to tumor antigens. More particularly, as described in Example 5, when used in a combination therapy there is a surprising synergy between flt3-L and a 4-1BB-L or antibodies to 4-1BB for anti-tumor immune responses. 4-1BB-L and antibodies reactive with 4-1BB are described in U.S. Pat. No. 5,674,704. The surprising synergy in the above described combination therapies for their ability to dramatically enhance anti-tumor immune responses suggests that stimulating more than one mechanism or more than one cell population is a promising approach to cancer treatment.

Additionally, interferon alpha, RANKL, or a CD30 ligand antagonist can be administered in combination with flt3-L to dramatically enhance immune responses. As described in Example 6, when used in a combination therapy there is a surprising synergy between flt3-L and interferon alpha for anti-tumor immune responses.

Other molecules that may be used in combination with flt3-L according to the present invention include IL-2, IL-12, IL-15, TRAIL, Fas ligand, VEGF antagonists, Tek antagonists, molecules that enhance dendritic cell function, survival, or expansion, molecules that enhance T cell activation or differentiation, molecules that enhance dendritic cell migration including various chemokines, molecules that increase the availability of target cell antigens, such as apoptotic factors and molecules that enhance MHC Class I presentation including the various interferons, angiogenesis inhibitors, inhibitors of immunosuppressive molecules released by tumors including IL-10, VEGF, and TGF-β, and tumor-specific antibodies including toxin- or radio-labeled antibodies.

In addition to stimulating an immune response to an antigen that already exists within the patient, flt3-ligand may be administered prior to, concurrently with or subsequent to administration of an antigen to a patient for immunization purposes. Thus, as a vaccine adjuvant, flt3-ligand can generate large quantities of dendritic cells in vivo to more effectively present the antigen. The overall response is a stronger and improved immune response and more effective immunization to the antigen. Further, flt3-L may be administered as a vaccine adjuvant in combination with additional active compounds prior to, concurrently with or subsequent to administration of an antigen to a patient for immunization purposes to enhance an immune response against tumor, viral or bacterial antigens. For example, CD40 binding proteins, such as CD40-L and antibodies to CD40 which enhance the ability of dendritic cells to present antigens to T cells can be administered in combination with flt3-L to dramatically enhance an immune response. Similarly, 4-1BB-L, antibodies reactive with 4-1BB, interferon alpha, RANKL, or CD30 ligand antagonists can be administered in combination with flt3-L to enhance an immune response and provide more effective immunization to the antigen.

The systemic administration of flt3-ligand not only is effective as a vaccine adjuvant, but as discussed supra., is effective in augmenting an immune response against previously existing antigens. For example, the inventors have shown that flt3-ligand administration to tumor-bearing mice results in at least a significant decrease in the growth rate of the tumor, and can result in tumor regression in a large proportion of the mice. The data are presented in more detail in Example 3. Flt3-L therefore is an important cytokine in the generation of an effective immune response in vivo against antigen. Data in Examples 4-6 demonstrate that when used in combination therapy with additional agents, flt3-L can provide a dramatically enhanced immune response in vivo against antigen.

Because of its ability to generate dendritic cells, flt3-ligand also finds use in promoting the survival of transplanted tissue or organs. When allogeneic organs or other tissue is transplanted into a host they can transfer stem cells, immature dendritic cells, and mature dendritic cells from the donor. These cells are called passenger cells and such cells can graft into the hematopoietic system of the host. Additionally, stem cells, immature dendritic cells, and mature dendritic cells from the host may graft to the donor organ or tissue. It is possible then to establish a tolerance between the graft and the host since the immature dendritic cells from the host and donor tissue interact with T-cells from the "other side." Such interaction may include the deletion of T-cells that recognize the major histocompatability complex (MHC) molecules that the dendritic cells express. In this way, the donor T cells are "screened" so that they fail to recognize and react against the host (i.e., no graft versus host disease) and the host T-cells are screened so that they fail to recognize and react against the graft (i.e., no graft rejection). Thus, a mutual tolerance can be achieved, and the graft is accepted. Administration of flt3-ligand to the host or donor prior to transplantation would generate increased numbers of dendritic cells in such host or donor and permit increased tolerance and survival of the graft.

For the growth and culture of dendritic cells, a variety of growth and culture media can be used, and the composition of such media can be readily determined by a person having ordinary skill in the art. Suitable growth media are solutions containing nutrients or metabolic additives, and include those that are serum-depleted or serum-based. Representative examples of growth media are RPMI, TC 199, Iscoves modified Dulbecco's medium (Iscove, et al., F.J. Exp. Med., 147:923 (1978)), DMEM, Fischer's, alpha medium, NCTC, F-10, Leibovitz's L-15, MEM and McCoy's. Particular examples of nutrients that will be readily apparent to the skilled artisan include, serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES, Tris, that act to stabilize the pH of the media, various inorganic salts. Particular reference is made to PCT Publ. No. WO 95/00632, wherein a variety of serum-free cellular growth media is described, such disclosure is incorporated herein by reference.

For any of the ex vivo methods of the invention, peripheral blood progenitor cells (PBPC) and peripheral blood stem cells (PBSC) are collected using apheresis procedures known in the art. See, for example, Bishop et al., *Blood*, vol. 83, No. 2, pp. 610-616 (1994). Briefly, PBPC and PBSC are collected using conventional devices, for example, a Haemonetics® Model V50 apheresis device (Haemonetics, Braintree, Mass.). Four-hour collections are performed typically no more than five times weekly until, for example, approximately $6.5 \times 10^8$ mononuclear cells (MNC)/kg patient are collected. The cells are suspended in standard media and then centrifuged to remove red blood cells and neutrophils. Cells located at the interface between the two phases (also known in the art as the buffy coat) are withdrawn and resuspended in HBSS. The suspended cells are predominantly mononuclear and a substantial portion of the cell mixture are early stem cells. The resulting stem cell suspension then can be contacted with biotinylated anti-CD34 monoclonal antibodies or other cell-binding means. The contacting period is maintained for a sufficient time to allow substantial interaction between the anti-CD34 monoclonal antibodies and the CD34 antigens on the stem cell surface. Typically, times of at least one hour are sufficient. The cell suspension then is brought into contact with the isolating means provided in the kit. The isolating means can comprise a column packed with avidin-coated beads. Such columns are well known in the art, see Berenson, et al., *J. Cell Biochem.*, 10D:239 (1986). The column is washed with a PBS solution to remove unbound material. Target stem cells can be released from the beads and from anti-CD34 monoclonal antibody using conventional methods. The stem cells obtained in this manner can be frozen in a controlled rate freezer (e.g., Cryo-Med®, Mt. Clemens, Mich.), then stored in the vapor phase of liquid nitrogen. Ten percent dimethylsulfoxide can be used as a cryoprotectant. After all collections from the donor have been made, the stem cells are thawed and pooled. Aliquots containing stem cells, growth medium, such as Mccoy's 5A medium, 0.3% agar, and at least one of the expansion factors: recombinant human GM-CSF, IL-3, recombinant human flt3-ligand, and recombinant human GM-CSF/IL-3 fusion molecules (PIXY321) at concentrations of approximately 200 U/mL, are cultured and expanded at 37° C. in 5% $CO_2$ in fully humidified air for 14 days. Optionally, human IL-1α or IL-4 may be added to the cultures. The most preferred combination of expansion factors comprises flt3-ligand plus either IL-3 or a GM-CSF/IL-3 fusion protein.

For in vivo administration to humans, flt3-ligand can be formulated according to known methods used to prepare pharmaceutically useful compositions. Flt3-L can be combined in admixture, either as the sole active material or with other known active materials (e.g. CD40 binding proteins, such as CD40-L or antibodies reactive with CD40, 4-1BB-L or antibodies reactive with 4-1BB, interferon alpha, RANKL, CD30 ligand antagonists), with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain flt3-ligand complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of flt3-ligand.

Flt3-L can be administered topically, parenterally, or by inhalation. The term "parenteral" includes subcutaneous injections, intravenous, intramuscular, intracisternal injection, or infusion techniques. These compositions will typically contain an effective amount of the flt3-ligand, alone or in combination with an effective amount of any other active material, e.g. those described above. Effective amounts, or dosages, and desired concentrations of flt3-L and active compounds (e.g. CD40-L and/or 4-1BB-L, antibodies reactive with 4-1BB, interferon alpha, RANKL, CD30 ligand antagonists) contained in the compositions may vary depending upon many factors, including the intended use, patient's body weight and age, and route of administration. Preliminary doses can be determined according to animal tests, and the scaling of dosages for human administration can be performed according to art-accepted practices. Keeping the above description in mind, typical dosages of flt3-ligand may range from about 10 μg per square meter to about 1000 μg per square meter. A preferred dose range is on the order of about 100 μg per square meter to about 300 μg per square meter.

In addition to the above, the following examples are provided to illustrate particular embodiments and not to limit the scope of the invention.

EXAMPLE 1

Generation of Dendritic Cells

This Example describes a method for using flt3-ligand to generate large numbers of dendritic cells ex vivo. Cells having the $CD34^+$ phenotype are isolated as described above, for example, first by generating a buffy coat of cells using a procedure described supra. Cells from the buffy coat are then incubated with a CD34 specific monoclonal antibody. The CD34+ cells which are selected then are cultured in McCoy's enhanced media with 20 ng/ml each of GM-CSF, IL-4, TNF-α, or 100 ng/ml flt3-ligand or c-kit ligand. The culture is continued for approximately two weeks at 37° C. in 10% $CO_2$ in humid air. Cells then are sorted by flow cytometry for CD1a+ and HLA-DR+ expression. The combination of GM-CSF, IL-4 and TNF-α, resulted in a six to seven-fold increase in the number of cells obtained after two weeks of culture. The combination of flt3-ligand and c-kit ligand resulted in an additive 12-13-fold increase in absolute cell numbers. This correlated with an 18-fold expansion with either flt3-ligand or c-kit ligand or to a 34-fold expansion with the combination of flt3-ligand and c-kit ligand. Phenotypic analysis of the cells showed that between 60-70% of the cells were HLA-DR+, CD86+, with 40-50% of the cells expressing CD1a in all factor combinations examined. The addition of flt3-ligand increased the absolute number of CD1a+ cells by 5-fold. c-Kit ligand increased those cells by 6.7-fold and the combination of flt3-ligand and c-kit ligand by 11-fold. Functional analysis of the resultant cells in an MLR revealed that the presence of flt3-ligand or c-kit ligand did not affect the stimulatory capacity of the resultant dendritic cells while increasing the numbers attained.

EXAMPLE 2

Use of Flt3-L in Dendritic Cell Expansion

This Example describes a method for using flt3-ligand for dendritic cell expansion. Prior to cell collection, it may be desirable to mobilize or increase the numbers of circulating PBPC and PBSC. Mobilization can improve PBPC and PBSC collection, and is achievable through the intravenous administration of flt3-ligand or sargramostim (Leukine®, Immunex Corporation, Seattle, Wash.) to the patients prior to collection of such cells. Other growth factors such as CSF-1, GM-CSF, c-kit ligand, G-CSF, EPO, IL-1, IL-2, IL-3, IL-4, IL-5, IL-6, IL-7, IL-8, IL-9, IL-10, IL-11, IL-12, IL-13, IL-14, IL-15, GM-CSF/IL-3 fusion proteins, LIF, FGF and combinations thereof, can be likewise administered in sequence, or in concurrent combination with flt3-ligand. Mobilized or non-mobilized PBPC and PBSC are collected using apheresis procedures known in the art. See, for example, Bishop et al., *Blood*, vol. 83, No. 2, pp. 610-616 (1994). Briefly, PBPC and PBSC are collected using conventional devices, for example, a Haemonetics® Model V50 apheresis device (Haemonetics, Braintree, Mass.). Four-hour collections are performed typically no more than five times weekly until approximately $6.5 \times 10^8$ mononuclear cells (MNC)/kg patient are collected. Aliquots of collected PBPC and PBSC are assayed for granulocyte-macrophage colony-forming unit (CFU-GM) content by diluting approximately 1:6 with Hank's balanced salt solution without calcium or magnesium (HBSS) and layering over lymphocyte separation medium (Organon Teknika, Durham, N.C.). Following centrifugation, MNC at the interface are collected, washed and resuspended in HBSS. One milliliter aliquots containing approximately 300,000 MNC, modified Mccoy's 5A medium, 0.3% agar, 200 U/mL recombinant human GM-CSF, 200 u/mL recombinant human IL-3, and 200 u/mL recombinant human G-CSF are cultured at 37° C. in 5% $CO_2$ in fully humidified air for 14 days. Optionally, flt3-ligand or GM-CSF/IL-3 fusion molecules (PIXY 321) may be added to the cultures. These cultures are stained with Wright's stain, and CFU-GM colonies are scored using a dissecting microscope (Ward et al., Exp. Hematol., 16:358 (1988). Alternatively, CFU-GM colonies can be assayed using the CD34/CD33 flow cytometry method of Siena et al., *Blood*, Vol. 77, No. 2, pp 400-409 (1991), or any other method known in the art.

CFU-GM containing cultures are frozen in a controlled rate freezer (e.g., Cryo-Med®, Mt. Clemens, Mich.), then stored in the vapor phase of liquid nitrogen. Ten percent dimethylsulfoxide can be used as a cryoprotectant. After all collections from the patient have been made, CFU-GM containing cultures are thawed and pooled. The thawed cell collection is contacted with flt3-ligand either alone, sequentially or in concurrent combination with other cytokines listed above. Such exposure to flt3-ligand will drive the CFU-GM to dendritic cell lineage. The dendritic cells are reinfused intravenously to the patient.

EXAMPLE 3

Use of Flt3-L in Augmenting Anti-tumor Immune Responses

This Example describes a method for using flt3-L to augment anti-tumor immune responses in vivo. Female C57BL/10J (B10) mice (The Jackson Laboratory, Bar Harbor, Me.) were injected with $5 \times 10^5$ viable B10.2 fibrosarcoma tumor cells by intradermal injection in a midline ventral position in a total volume of 50 µl. The fibrosarcoma B10.2 line is of B10 origin and has been described previously, see Lynch et a., *Euro. J Immunol.*, 21:1403 (1991) incorporated herein by reference. The fibrosarcoma B10.2 line was induced by subcutaneous implantation of a paraffin pellet containing 5 mg of methylcholanthrene. The tumor cell line was maintained in vitro in α- modified MEM containing 5% FBS, 2 nM L-glutamine, 50U/ml penicillin and 50 µg/ml streptomycin. Recombinant human flt3-L (10 µg/injection) was administered on a daily basis over a 19-day period (unless otherwise noted) by subcutaneous injection in a total volume of 100 µl. Control mice were similarly injected with a similar volume of buffer containing 100 ng MSA. Tumor growth rates were determined by plotting the tumor size versus time after tumor challenge. Tumor size was calculated as the product of two perpendicular diameters, measured by calipers, and is expressed as the mean tumor size of only those mice bearing a tumor within a particular treatment group. The number of mice bearing tumors compared to the number challenged for each treatment group at the termination of an experiment are shown in the data below.

From Table I, the data is a compilation of six different experiments wherein B10.2 tumor-bearing mice were either treated with flt3-ligand or MSA. Complete tumor regression was observed in 19 of 50 flt3-ligand treated mice compared to 1 of 30 in MSA-treated mice (p<0.0001 using Fishers Exact Test). The rate of tumor growth in flt3-ligand treated mice (mean tumor size in tumor-bearing mice at week 5 post-tumor challenge was 60+/−8 $mm^2$) was significantly reduced (p.0001 by Analysis of Variance) compared to MSA-treated mice (mean tumor size at week 5 post-tumor challenge was 185+/−17 $mm^2$).

TABLE I

B10.2 Fibrosarcoma +/− Flt3-L Composite of Six Experiments
Tumor Size (mm$^2$)

| Weeks Post Tumor Challenge | MSA Control (100 ng/day) | Standard Error | Flt3-L (10 µg/day) | Standard Error |
|---|---|---|---|---|
| 0 | 0 | 0 | 0 | 0 |
| 1 | 25 | 2.6 | 24 | 2.2 |
| 2 | 62 | 7.5 | 49 | 3.6 |
| 3 | 98 | 10.6 | 49 | 3.9 |
| 4 | 149 | 14.5 | 50 | 5 |
| 5 | 185 | 16.8 | 60 | 8.4 |

Tumor size was sharply retarded with flt3-L compared to the control. Therefore, the data show that flt3-L is an important cytokine in the augmentation of the immune response against tumor and foreign antigens, and in particular against cancer.

EXAMPLE 4

Use of Flt3-L in Combination Therapy to Activate an Immune Response

This Example demonstrates the use of flt3-L in combination with a CD40 binding protein to augment anti-tumor immune responses in vivo. In one study C57BL/10J (B10) mice (The Jackson Laboratory, Bar Harbor, Me.) were injected intradermally with 5×10$^5$ cells of the viable B10.2 fibrosarcoma tumor cell line described in Example 3 above, and the mice were subdivided into four sets each containing eight mice. In one set of mice, beginning on the same day as the tumor injections, recombinant human flt3-L (10 µg/injection/day) was administered to each mouse on a daily basis over a 20-day period by subcutaneous injection in a total volume of 100 µl. In another set of mice each mouse was injected with the same volume and amount of CD40-L each day for 20 days. In a third set, each mouse was injected with a combination of 10 µg flt3-L and 10 µg of CD40-L per day for 20 days. Control mice were similarly injected with a similar volume of buffer containing 100 ng MSA. Tumor growth rates were determined measuring tumor size each week after tumor challenge over a 6 week period. Tumor size was calculated as the product of two perpendicular diameters, measured by calipers, and is expressed as the mean tumor size. Only mice bearing tumors within each group were considered in determining the mean size. The frequency of tumor rejections was also determined and expressed as the number of mice bearing no tumors compared to the number challenged for each treatment group at the termination of an experiment.

Table II provides data in the form of mean tumor size in tumor bearing animals, calculated once a week over a 6 week period post challenge. Table III details the percent frequency of tumor rejection for each set of mice over a 6 week period post challenge. The data demonstrate that for tumor bearing mice, the mean tumor size mice in mice treated with flt3-L and flt3-L in combination with CD40-L is comparable and less than the tumor size in tumor bearing control mice. Significantly, however, mice receiving the combination therapy experienced significantly higher frequency of tumor rejection than mice receiving flt3-L or CD40-L alone. More specifically, 6 weeks post challenge, 62.5% of the mice receiving the combination therapy experienced complete tumor rejection. By contrast, at 6 weeks post challenge, 25% of the mice receiving flt3-L alone experienced complete tumor rejection and none of the mice receiving CD40-L alone or MSA experienced complete tumor rejection.

TABLE II

B10.2 Fibrosarcoma
Tumor Size (mm$^2$)

| Weeks Post Tumor Challenge | MSA Control (100 ng/day) | Flt3-L (10 µg/day) | CD40-L (10 µg/day) | Flt3-L/CD40-L (each 10 µg/day) |
|---|---|---|---|---|
| 1 | 28 | 24 | 25 | 23 |
| 2 | 68 | 51 | 62 | 46 |
| 3 | 135 | 64 | 107 | 59 |
| 4 | 239 | 81 | 212 | 80 |
| 5 | 351 | 117 | 343 | 137 |
| 6 | 482 | 159 | 493 | 213 |

TABLE III

B10.2 Fibrosarcoma
% Frequency of Tumor Rejection

| Weeks Post Tumor Challenge | MSA Control (100 ng/day) | Flt3-L (10 µg/day) | CD40-L (10 µg/day) | Flt3-L/CD40-L (each 10 µg/day) |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 12.5 | 0 | 50 |
| 5 | 0 | 25 | 0 | 62.5 |
| 6 | 0 | 25 | 0 | 62.5 |

In another study C3H/HeN mice were injected intradermally with 5×10$^5$ cells of a very aggressive tumor, the 87 fibrosarcoma tumor cell line (generated by chronic exposure of C3H/HeN(MTV−) mice to ultraviolet radiation). The mice were then subdivided into four sets, each containing ten mice. In one set of mice, beginning the day after the tumor injections, recombinant human flt3-L (10 µg/injection/day) was administered to each mouse on a daily basis over a 20-day period by subcutaneous injection. In another set of mice, each mouse was injected with the same volume and amount of CD40-L each day, beginning at day 7 and continuing to day 20. In a third set, each mouse received a combination therapy of CD40-L and flt3-L. The combination therapy included 10 µg/day of flt3-L beginning the day after tumor injection and continuing until day 20 and 10 µg/day of CD40-L beginning at day 7 and continuing until day 20. Mice in a control group were similarly injected with a similar volume of buffer containing 100 ng MSA. Tumor growth rates were determined by measuring tumor size each week post tumor challenge over a 6 week period. Tumor size was calculated as the product of two perpendicular diameters, measured by calipers, and is expressed as the mean tumor size. Only mice bearing tumors were considered in determining the mean size. The frequency of tumor rejections was also determine and expressed as the number of mice bearing no tumors compared to the number challenged for each treatment group at the termination of an experiment.

Table IV provides data in the form of mean tumor size in tumor bearing animals, calculated once a week over a 6 week period post challenge. Table V details the percent frequency of tumor rejection for each set of mice over a 6 week period post challenge. The data demonstrate that for tumor bearing mice, the mean tumor size mice in mice treated with flt3-L in combination with CD40-L is significantly less than the tumor size in tumor bearing control mice and mice bearing tumors in the groups receiving only flt3-L and only CD40-L. Significantly, mice receiving the combination therapy experienced significantly higher frequency of tumor rejection than mice receiving. flt3-L or CD40-L alone. More specifically, 6 weeks post challenge, 50% of the mice receiving the combination therapy experienced complete tumor rejection. By contrast, at 6 weeks post challenge, 10% of the mice receiving flt3-L alone experienced complete tumor rejection and none of the mice receiving CD40-L alone or MSA experienced complete tumor rejection.

The observations described above demonstrate that a flt3-L and CD40-L combination therapy can dramatically up-regulate anti-tumor immune responses in vivo. The data indicate that a synergy exists between flt3-L and the CD40 binding protein, CD40-L, in that when used alone flt3-L and CD40-L show little or no tumor rejection. In combination the rejection is dramatic. In addition to synergy, studies indicated that the combination of CD40-L and flt3-L induced expression of IL-12 mRNA in the tumors.

TABLE IV

87 Fibrosarcoma
Tumor Size (mm$^2$)

| Weeks Post Tumor Challenge | MSA Control (100 ng/day) | Flt3-L (10 µg/day) | CD40-L (10 µg/day) | Flt3-L/CD40-L (each 10 µg/day) |
|---|---|---|---|---|
| 1 | 23 | 23 | 30 | 29 |
| 2 | 54 | 53 | 49 | 34 |
| 3 | 108 | 94 | 87 | 44 |
| 4 | 176 | 159 | 144 | 67 |
| 5 | 286 | 256 | 247 | 115 |
| 6 | 465 | 439 | 410 | 239 |

TABLE V

87 Fibrosarcoma
% Frequency of Tumor Rejection

| Weeks Post Tumor Challenge | MSA Control (100 ng/day) | Flt3-L (10 µg/day) | CD40-L (10 µg/day) | Flt3-L/CD40-L (each 10 µg/day) |
|---|---|---|---|---|
| 1 | 0 | 0 | 0 | 0 |
| 2 | 0 | 0 | 0 | 0 |
| 3 | 0 | 0 | 0 | 30 |
| 4 | 0 | 10 | 0 | 40 |
| 5 | 0 | 10 | 0 | 50 |
| 6 | 0 | 10 | 0 | 50 |

EXAMPLE 5

Use of Flt3-L in Combination Therapy to Activate an Immune Response

This Example demonstrates the use of flt3-L in combination with an antibody reactive with 4-1BB to augment anti-tumor immune responses in vivo. In one study C57BL/10J (B10) mice (The Jackson Laboratory, Bar Harbor, Me.) were injected intradermally with 5×10$^5$ cells of the viable B10.2 fibrosarcoma tumor cell line described in Example 3 above. In one set of mice, beginning on the same day as the tumor injections, recombinant human flt3-L (10 µg/injection/day) was administered to each mouse on a daily basis over a 14-day period by subcutaneous injection in a total volume of 100 µl. In another set of mice each mouse was injected IP with 100 µg of rat anti mu 4-1BB (clone m6) on days 3 and 6 post tumor challenge. In a third set, each mouse was injected with 100 µg rat anti mu 4-1BB clone m6 on days 13 and 16. A fourth set of mice were injected with a combination of 10 µg flt3-L on days 1-14 and 100 µg of rat anti mu 4-1BB clone m6 on days 13 and 16 post tumor challenge. Control mice were injected with buffer containing 100 ng MSA. Tumor growth rates were determined measuring tumor size each week after tumor challenge over a 5 week period. Tumor size was calculated as the product of two perpendicular diameters, measured by calipers, and is expressed as the mean tumor size in mm$^2$. Only mice bearing tumors within each group were considered in determining the mean tumor size. The percent incidence of tumors was also determine and expressed as the number of mice bearing tumors compared to the number challenged for each treatment group at the termination of an experiment.

Table VI provides data in the form of mean tumor size in tumor bearing animals, calculated once a week over an 8 week period post challenge. Table VII details the percent incidence of tumors for each set of mice over an 8 week period post challenge. The data demonstrate that for tumor bearing mice, the mean tumor size in mice treated with flt3-L alone and the mean tumor size in mice treated with the anti 4-1BB regimen are similar. However, when flt3-L in combination with an antibody reactive with 4-1BB is administered to mice, mean tumor size in tumor bearing mice is remarkably decreased. Specifically, at 5 weeks post tumor challenge, mice receiving the combination therapy had a mean tumor size of 0, indicating 100% tumor rejection. This data is supported by the numbers in Table VII which demonstrate that mice receiving the combination therapy experienced significantly lower incidence of tumors than mice receiving flt3-L or 4-1BB antibody alone. More specifically, at 5 weeks post challenge, all of the mice receiving the combination therapy experienced complete tumor rejection (0% tumor incidence). By contrast, at 5 weeks post challenge, 70% of the mice receiving flt3-L alone had tumors and 50% and 70% of the mice receiving 4-1BB antibody alone had tumors. This data provides evidence that anti-4-1BB synergizes with flt3-L in enhancing immune response.

TABLE VI

B10.2 Fibrosarcoma
Tumor Size (mm$^2$)

| Weeks Post Tumor Challenge | MSA Control (100 ng/day) | Flt3-L (10 µg/day) | anti 4-1BB (100 µg, day 3 and 6) | anti 4-1BB (100 µg days 13 and 16) | anti 4-1BB (days 13 and 16) and flt3-L |
|---|---|---|---|---|---|
| 1 | 28 | 15 | 25 | 25 | 20 |
| 2 | 60 | 35 | 55 | 60 | 35 |
| 3 | 85 | 35 | 55 | 40 | 15 |
| 4 | 125 | 45 | 60 | 50 | 8 |
| 5 | 200 | 55 | 70 | 40 | 0 |
| 6 | 280 | 95 | 80 | 45 | 0 |
| 7 | | 125 | 130 | 115 | 0 |
| 8 | | | 160 | 135 | 0 |

TABLE VII

B10.2 Fibrosarcoma
% Tumor Incidence

| Weeks Post Tumor Challenge | MSA Control (100 ng/day) | Flt3-L (10 µg/day) | anti 4-1BB (days 3 and 6) | anti 4-1BB (days 13 and 16) | Flt3-L and anti 4-1BB (days 13 and 16) |
|---|---|---|---|---|---|
| 1 | 100 | 100 | 100 | 100 | 100 |
| 2 | 100 | 100 | 100 | 100 | 90 |
| 3 | 100 | 100 | 90 | 100 | 80 |
| 4 | 100 | 90 | 80 | 50 | 30 |
| 5 | 100 | 70 | 70 | 50 | 0 |
| 6 | 100 | 60 | 60 | 40 | 0 |
| 7 | 100 | 60 | 50 | 20 | 0 |
| 8 | 100 | 60 | 50 | 20 | 0 |

EXAMPLE 6

Use of Flt3-L in Combination Therapy to Activate an Immune Response

This Example demonstrates the use of flt3-L in combination with interferon alpha augment anti-tumor immune responses in vivo. In one study the B10.2 fibrosacoma tumor cell line (described in Example 3 above) was implanted in C57BL/10J (B10) mice on day 0. One set of mice (n=10) was treated with recombinant human flt3-L (50 µg/day, by subcutaneous injection) on days 10 to 29 post tumor challenge. Another set of mice (n=5) was treated with human interferon alpha (interferon alpha A/D; 60,000 U/day, by subcutaneous injection) on days 21 to 25 post tumor challenge. A third set of mice (n=5) was treated with flt3-L on days 10 to 29 and also with interferon alpha on days 21 to 25. Control mice were injected with buffer containing 100 ng MSA. Tumor growth rates were determined by measuring tumor size over a 7 week period. Tumor size was calculated as the product of two perpendicular diameters, measured by calipers, and is expressed as the mean tumor size in mm$^2$. Only mice bearing tumors within each group were considered in determining the mean tumor size. The percent incidence of tumors was also determined (i.e., the number of mice bearing tumors compared to the number challenged) for each treatment group.

Table VIII shows the mean tumor size in tumor bearing animals, and Table IX shows the percent incidence of tumors. This data demonstrates that interferon alpha synergizes with flt3-L in enhancing immune response in the B10.2 tumor model. Most significantly, the tumor rejection rate was 40% for flt3-L alone and 80% for the combination of flt3-L and interferon alpha.

TABLE VIII

B10.2 Fibrosarcoma
Tumor size (mm$^2$)

| Days Post Tumor Challenge | MSA (100 ng/day) (n = 10) | Flt3L (50 µg/day, days 1-20) (n = 10) | IFNα (60 K U/day, days 11-15) (n = 5) | FL + IFNα (n = 5) |
|---|---|---|---|---|
| 7 | 17 | 16 | 16 | 16 |
| 14 | 42 | 43 | 46 | 41 |
| 21 | 71 | 76 | 77 | 69 |
| 28 | 125 | 107 | 125 | 101 |
| 35 | 183 | 126 | 198 | 90 |
| 42 | 238 | 131 | 267 | 55 |
| 49 | 322 | 219 | 364 | 186 |

TABLE IX

B10.2 Fibrosarcoma
% Tumor incidence

| Days Post Tumor Challenge | MSA (100 ng/day) (n = 10) | Flt3L (50 µg/day, days 1-20) (n = 10) | IFNα (60 K U/day, days 11-15) (n = 5) | FL + IFNα (n = 5) |
|---|---|---|---|---|
| 7 | 100 | 100 | 100 | 100 |
| 14 | 100 | 100 | 100 | 100 |
| 21 | 100 | 100 | 100 | 80 |
| 28 | 100 | 100 | 100 | 80 |
| 35 | 100 | 100 | 100 | 80 |
| 42 | 100 | 80 | 100 | 60 |
| 49 | 100 | 60 | 100 | 20 |

What is claimed is:

1. A method for treating a fibrosarcoma in a human patient, comprising administering to a human patient having a fibrosarcoma, a composition comprising an effective amount of Flt3-ligand, wherein the Flt3-ligand comprises an amino acid sequence that is at least 90% identical to amino acids 28 to Xaa of SEQ ID NO:2, wherein Xaa is an amino acid from 160 to 235, and wherein said Flt3-ligand binds Flt-3, wherein said composition does not contain GM-CSF.

2. The method of claim 1, wherein the Flt3-ligand stimulates the proliferation of hematopoietic stem or progenitor cells.

3. The method of claim 1, wherein the Flt3-ligand stimulates the proliferation of cells selected from the group consisting of myeloid precursor cells, monocytic cells, macrophages, B-cells and dendritic cells.

4. A method of increasing the number of dendritic cells in a human patient having a fibrosarcoma, comprising administering to said human patient, a composition comprising Flt3-ligand in an amount sufficient to increase the number of dendritic cells is said patient, wherein the Flt3-ligand comprises an amino acid sequence that is at least 90% identical to amino acids 28 to Xaa of SEQ ID NO:2, wherein Xaa is an amino acid from 160 to 235, and wherein said Flt3-ligand binds Flt-3, wherein said composition does not contain GM-CSF.

5. A method of augmenting fibrosarcoma-specific immune responses in a human patient having a fibrosarcoma, comprising administering to said human patient, a composition comprising an effective amount of Flt3-ligand, wherein the Flt3-ligand comprises an amino acid sequence that is at least 90% identical to amino acids 28 to Xaa of SEQ ID NO:2, wherein Xaa is an amino acid from 160 to 235, and wherein said Flt3-ligand binds Flt-3, wherein said composition does not contain GM-CSF.

6. A method of reducing fibrosarcoma growth in a human patient having a fibrosarcoma, comprising administering to said human patient, a composition comprising an effective amount of Flt3-ligand, wherein the Flt3-ligand comprises an amino acid sequence that is at least 90% identical to amino acids 28 to Xaa of SEQ ID NO:2, wherein Xaa is an amino acid from 160 to 235, and wherein said Flt3-ligand binds Flt-3, wherein said composition does not contain GM-CSF.

7. A method of reducing fibrosarcoma incidence in a human patient having a fibrosarcoma, comprising administering to said human patient, a composition comprising an effective amount of Flt3-ligand, wherein the Flt3-ligand comprises an amino acid sequence that is at least 90% identical to amino acids 28 to Xaa of SEQ ID NO:2, wherein Xaa is an amino acid from 160 to 235, and wherein said Flt3-ligand binds Flt-3, wherein said composition does not contain GM-CSF.

8. A method of increasing fibrosarcoma rejection in a human patient having a fibrosarcoma, comprising administering to said human patient, a composition comprising an effective amount of Flt3-ligand, wherein the Flt3-ligand comprises an amino acid sequence that is at least 90% identical to amino acids 28 to Xaa of SEQ ID NO:2, wherein Xaa is an amino acid from 160 to 235, and wherein said Flt3-ligand binds Flt-3, wherein said composition does not contain GM-CSF.

9. The method of claim 1, wherein the Flt3-ligand is human Flt3-ligand.

10. The method of claim 1, wherein the Flt3-ligand is soluble human Flt3-ligand.

11. The method of claim 1, wherein the Flt3-ligand comprises amino acids 28 to Xaa of SEQ ID NO:2, wherein Xaa is an amino acid from 160 to 235.

12. The method of claim 1, wherein the Flt3-ligand comprises amino acid residues 28-160 of SEQ ID NO:2.

13. The method of claim 1, wherein the Flt3-ligand comprises amino acid residues 28-182 of SEQ ID NO:2.

14. The method of claim 1, wherein the composition further comprises a pharmaceutically suitable carrier, diluent and/or preservative.

15. The method of claim 1, wherein the Flt3-ligand is complexed with polyethylene glycol.

16. The method of claim 1, wherein the Flt3-ligand is administered topically, parenterally or by inhalation.

* * * * *

SEQUENCE LISTING

<160> NUMBER OF SEQ ID NOS: 2

<210> SEQ ID NO 1
<211> LENGTH: 988
<212> TYPE: DNA
<213> ORGANISM: homo sapiens
<220> FEATURE:
<221> NAME/KEY: CDS
<222> LOCATION: (30)..(734)
<223> OTHER INFORMATION:

-continued

<400> SEQUENCE: 1

```
cggccggaat tccggggccc ccggccgaa atg aca gtg ctg gcg cca gcc tgg    53
                                Met Thr Val Leu Ala Pro Ala Trp
                                 1               5 agc cca aca acc tat ctc ctc ctg ctg ctg ctg agc tcg gga ctc        101
Ser Pro Thr Thr Tyr Leu Leu Leu Leu Leu Leu Ser Ser Gly Leu
     10                  15                  20 agt ggg acc cag gac tgc tcc ttc caa cac agc ccc atc tcc tcc gac    149
Ser Gly Thr Gln Asp Cys Ser Phe Gln His Ser Pro Ile Ser Ser Asp
 25                  30                  35                  40 ttc gct gtc aaa atc cgt gag ctg tct gac tac ctg ctt caa gat tac    197
Phe Ala Val Lys Ile Arg Glu Leu Ser Asp Tyr Leu Leu Gln Asp Tyr
                 45                  50                  55 cca gtc acc gtg gcc tcc aac ctg cag gac gag gag ctc tgc ggg ggc    245
Pro Val Thr Val Ala Ser Asn Leu Gln Asp Glu Glu Leu Cys Gly Gly
             60                  65                  70 ctc tgg cgg ctg gtc ctg gca cag cgc tgg atg gag cgg ctc aag act    293
Leu Trp Arg Leu Val Leu Ala Gln Arg Trp Met Glu Arg Leu Lys Thr
         75                  80                  85 gtc gct ggg tcc aag atg caa ggc ttg ctg gag cgc gtg aac acg gag    341
Val Ala Gly Ser Lys Met Gln Gly Leu Leu Glu Arg Val Asn Thr Glu
     90                  95                 100 ata cac ttt gtc acc aaa tgt gcc ttt cag ccc ccc ccc agc tgt ctt    389
Ile His Phe Val Thr Lys Cys Ala Phe Gln Pro Pro Pro Ser Cys Leu
105                 110                 115                 120 cgc ttc gtc cag acc aac atc tcc cgc ctc ctg cag gag acc tcc gag    437
Arg Phe Val Gln Thr Asn Ile Ser Arg Leu Leu Gln Glu Thr Ser Glu
                125                 130                 135 cag ctg gtg gcg ctg aag ccc tgg atc act cgc cag aac ttc tcc cgg    485
Gln Leu Val Ala Leu Lys Pro Trp Ile Thr Arg Gln Asn Phe Ser Arg
            140                 145                 150 tgc ctg gag ctg cag tgt cag ccc gac tcc tca acc ctg cca ccc cca    533
Cys Leu Glu Leu Gln Cys Gln Pro Asp Ser Ser Thr Leu Pro Pro Pro
        155                 160                 165 tgg agt ccc cgg ccc ctg gag gcc aca gcc cgg aca gcc cgg cag ccc    581
Trp Ser Pro Arg Pro Leu Glu Ala Thr Ala Pro Thr Ala Pro Gln Pro
    170                 175                 180 cct ctc ctc cta ctg ctg ctg ccc gtg ggc ctc ctg ctg gcc             629
Pro Leu Leu Leu Leu Leu Leu Leu Pro Val Gly Leu Leu Leu Ala
185                 190                 195                 200 gct gcc tgg tgc ctg cac tgg cag agg acg cgg cgg agg aca ccc cgc    677
Ala Ala Trp Cys Leu His Trp Gln Arg Thr Arg Arg Arg Thr Pro Arg
                205                 210                 215 cct ggg gag cag gtg ccc ccc gtc ccc agt ccc cag gac ctg ctg ctt    725
Pro Gly Glu Gln Val Pro Pro Val Pro Ser Pro Gln Asp Leu Leu Leu
            220                 225                 230 gtg gag cac tgacctggcc aaggcctcat cctgcggagc cttaaacaac            774
Val Glu His
        235 gcagtgagac agacatctat catcccattt tacagggagg gatactgagg cacacagagg  834 ggagtcacca gccagaggat gtatagcctg gacacagagg aagttggcta gaggccggtc  894 ccttccttgg gccctctca ttccctcccc agaatggagg caacgccaga atccagcacc   954 ggccccattt acccaactct gaacaaagcc ccg                               988
```

<210> SEQ ID NO 2
<211> LENGTH: 235
<212> TYPE: PRT

```
<213> ORGANISM: homo sapiens

<400> SEQUENCE: 2

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
                100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
            165                 170                 175

Thr Ala Pro Thr Ala Pro Gln Pro Pro Leu Leu Leu Leu Leu Leu Leu
            180                 185                 190

Pro Val Gly Leu Leu Leu Leu Ala Ala Ala Trp Cys Leu His Trp Gln
        195                 200                 205

Arg Thr Arg Arg Arg Thr Pro Arg Pro Gly Glu Gln Val Pro Pro Val
        210                 215                 220

Pro Ser Pro Gln Asp Leu Leu Leu Val Glu His
225                 230                 235
```